United States Patent [19]

Kwasman

[11] 4,163,615

[45] Aug. 7, 1979

[54] READER FOR HEMATOCRIT VALUE

[76] Inventor: Alan Kwasman, 6239 Morse Ave., North Hollywood, Calif. 91606

[21] Appl. No.: 844,964

[22] Filed: Oct. 25, 1977

[51] Int. Cl.² ................. G01N 33/16; G01B 11/00
[52] U.S. Cl. ................................. 356/39; 350/115; 356/40; 356/383; 356/397
[58] Field of Search .............. 356/39, 40, 157, 164, 356/165, 166, 171, 379, 383, 397; 350/114, 115

[56] References Cited

U.S. PATENT DOCUMENTS 2,731,725  1/1956  Stefacek ........................ 356/171
2,911,879  11/1959  Giwosky ........................ 356/171

FOREIGN PATENT DOCUMENTS 937335  8/1948  France ........................ 356/39

Primary Examiner—Vincent P. McGraw
Attorney, Agent, or Firm—Gilbert Kivenson

[57] ABSTRACT

A device permitting the rapid and direct determination of red cell percentages in centrifuged blood samples comprised of a scale optically variable in length in combination with an adjustable holder for the blood containing capillary tube.

4 Claims, 4 Drawing Figures

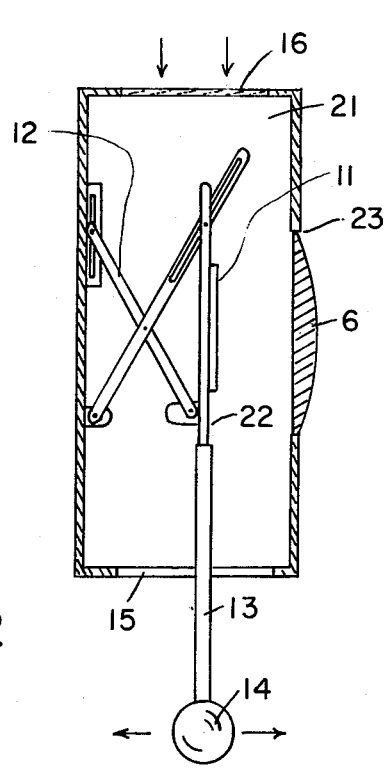
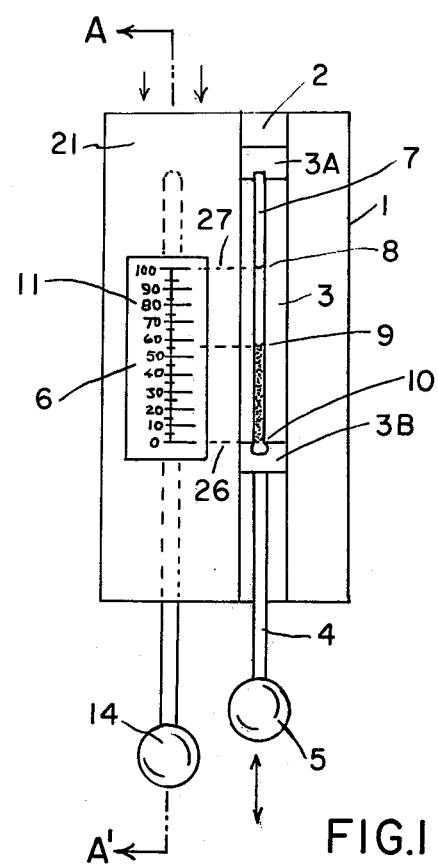
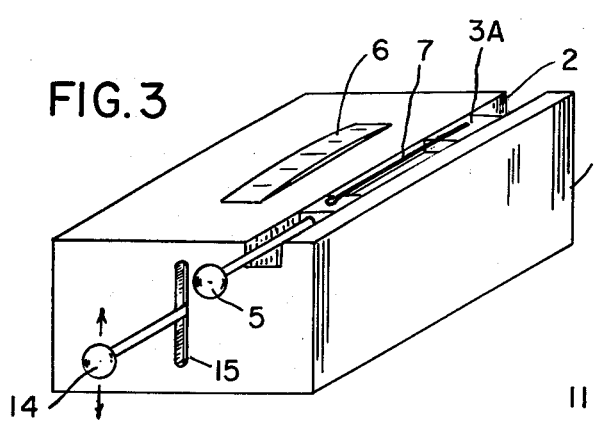
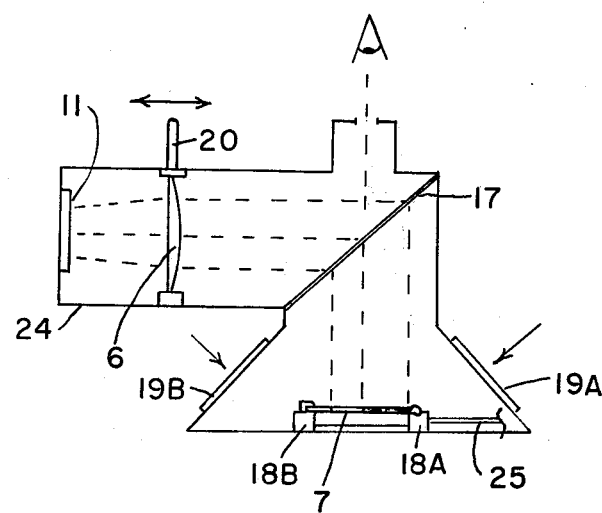
FIG. 2
FIG. 1
FIG. 3
FIG. 4

READER FOR HEMATOCRIT VALUE

BACKGROUND OF THE INVENTION

The present invention relates to an apparatus for quickly determining the percentage of red cells in a blood sample which has been sedimented in a capillary tube. Sedimentation of red cells is usually accomplished by drawing a sample of whole blood into a capillary tube, sealing the tube at one end and subjecting it to centrifugal force directed towards the closed end. The red cells, being heavier than the plasma, form a pack at the closed end of the tube with a visible interface between the cells and the clear liquid. The percentage of red cell content is determined by dividing the length of red cell pack by the overall length of the sample and multiplying the quotient by 100. The overall length varies so that two separate length measurements are required.

It is an object of the present invention to simplify these measurements and thus facilitate the determination of red cell content. It is another object of the invention to permit a non-skilled person to make red cell determinations with a minimum of training. It is a further object of the invention to provide a simpler and relatively inexpensive device, compared for example, to the logarithmic scale unit presently used and a more accurate method than the divergent graphs heretofore employed.

DESCRIPTION OF THE INVENTION

The present invention makes use of an optically expandable scale which is so adjusted that its overall length matches that of the blood sample. The scale is linearly divided into 100 parts and fractions thereof so that it is a simple matter to read the red cell level as a percentage of the overall length.

A detailed description of the operation of the invention will be made in the following paragraphs and in reference to the accompanying drawings. The following is a description of the drawings:

FIG. 1 is a plan view of one embodiment of the invention.

FIG. 2 is a cut away view of FIG. 1 taken along the section A—A'.

FIG. 3 is an isometric view of the invention.

FIG. 4 is a schematic cut-away of a second embodiment of the invention.

Referring now to FIG. 1 it will be seen that the device is contained in a rectangular housing 1. A slit 2 is cut into the housing 1. Slidably mounted in slit 2 is a capillary tube carrier 3 comprised of raised sections 3A and 3B which are grooved to receive blood sample tube 7. The carrier 3 can be slid along the slot 2 and can be positioned at any point along the slit 2 by the use of extension 4 and the knob 5. The chamber 21, also shown in cross section in FIG. 2, contains a scale 11 firmly mounted on a surface 22 which is constrained to linear movement by the linkage 12. The surface 22 can be positioned at any point along a linear path by the extension 13 and knob 14. Chamber 21 contains 3 openings. The opening 23 is sealed by the magnifier 6. When the user views scale 11 through magnifier 6, he sees a virtual image of the scale which can be varied in length as the knob 14 is moved through its range of travel. A second opening 16 in chamber 21 is sealed by a transparent material and serves to illuminate scale 11 using external light as a source. The third opening in chamber 21 is the slit 15 which allows the extension 13 to be moved freely in the directions shown in FIGS. 2 and 3.

The operation of the invention is as follows: the capillary tube containing the centrifuged blood sample is first placed in carrier 3 between the raised sections 3A and 3B. Carrier 3 is adjusted by use of the knob 5 until the entire length of the blood sample is within the boundaries of the openings 23 as is shown by the dotted lines 26 and 27 in FIG. 1. The knob 14 is now manipulated so that the length of scale 11 as seen through magnifier 6 is equal to the distance between levels 8 and 10 of the capillary tube 7. In practice it is necessary to move both knob 5 and knob 14 to adjust the apparent length of scale 11 and to position the capillary tube properly. When this has been done, the position of the interface between clear plasma and the red cells, level 9 in FIG. 1, is read from the scale. The reading gives the percentage of red cells in the sample and no computation is required. In FIG. 1, by way of illustration, the sample would indicate a red cell content of 56 percent.

A number of features of the device as described above can be altered without departing from the spirit of the invention. The magnifier 6 may, for example, be in the form of a cylindrical lens or in the form of a relatively flat Fresnel lens. Various other lens shapes and configurations may be used to reduce aberration when high accuracy is desired. Other kinds of scale moving mechanisms other than the linkage 12 of FIG. 2 may be used. Illumination of the scale or capillary tube may be done with small electric bulbs. Non-linear or special scales might be employed for special applications. Although the device has been described with reference to blood cell determination, it can be readily modified for other measurements such as those encountered in chromatography.

A second embodiment of the invention is shown in FIG. 4. An essential feature of this embodiment is the transparent plate 17. A variable size image of the scale 11 is seen by the observer as a reflection from plate 17. He is also able to see the capillary tube 7. Windows 19 and 19A help illuminate the capillary tube. The instrument housing 24 is constructed of transparent material to allow external light to illuminate the scale. Scale size is adjusted by magnifier 6 which is moved horizontally by knob 20. The capillary is positioned by extension 25. In this embodiment the image of the scale is superimposed on that of the capillary so that adjustment and reading are facilitated.

The device is simple in construction and can be operated by relatively unskilled individuals after very little training. It will permit a large number of readings to be made in a short time.

What is claimed is as follows:

1. A device for determining the sedimented red cell percentage of a blood sample centrifuged in a capillary tube comprising an adjustable holding means for said capillary tube and means for producing a variable sized image of a percentage scale in close proximity to said capillary tube whereby adjustment of said image to match the linear size of said blood sample permits direct reading of sedimented red blood percentage.

2. A device for determining the sedimented red cell percentage of a blood sample as set forth in claim 1 wherein said holding means is a slidably mounted clamp containing grooves for holding said capillary tube.

3. A device for determining the sedimented red cell percentage of a blood sample as set forth in claim 1 wherein said means for producing a variable sized image is comprised of a fixed magnifier and a linearly divided percentage scale which is constrained to move perpendicularly to said magnifier whereby said image will change in length as seen through the magnifier as the scale distance to the magnifier is varied and wherein said image can be used to determine the relative length of said sedimented red cells as a percentage of the total length of the blood sample in said capillary tube.

4. A device for determining the sedimented red cell percentage of a blood sample as set forth in claim 1 wherein said means for producing a variable sized image is comprised of a fixed scale and moveable magnifier and a semi-reflecting, obliquely positioned, transparent plate whereby an image of said percentage scale is seen superimposed on a view of said capillary tube transmitted through said transparent plate.

* * * * *